(12) United States Patent
Gissmann et al.

(10) Patent No.: US 7,320,861 B2
(45) Date of Patent: Jan. 22, 2008

(54) POLYVALENT VACCINE AGAINST DISEASES CAUSED BY PAPILLOMA VIRUSES, METHOD FOR THE PRODUCTION AND THE USE THEREOF

(75) Inventors: Lutz Gissmann, Wiesloch (DE); Kai Pohlmeyer, Fitzbek (DE); Martin Müller, Neckargemünd (DE)

(73) Assignee: Deutsches Krebsforschungszentrum Stiftung des Oeffentlichen Rechts, Heidelberg (DE)

( * ) Notice: Subject to any disclaimer, the term of this patent is extended or adjusted under 35 U.S.C. 154(b) by 294 days.

(21) Appl. No.: 10/485,454

(22) PCT Filed: Jul. 26, 2002

(86) PCT No.: PCT/EP02/08360

§ 371 (c)(1),
(2), (4) Date: Aug. 31, 2004

(87) PCT Pub. No.: WO03/011335

PCT Pub. Date: Feb. 13, 2003

(65) Prior Publication Data

US 2005/0004054 A1    Jan. 6, 2005

(30) Foreign Application Priority Data

Jul. 30, 2001   (DE) ................. 101 37 102

(51) Int. Cl.
*C12Q 1/68*   (2006.01)
(52) U.S. Cl. .................. 435/6; 435/345; 435/69.1
(58) Field of Classification Search .............. 435/6, 435/69.1, 91.1, 345
See application file for complete search history.

(56) References Cited

U.S. PATENT DOCUMENTS 4,551,270 A   11/1985   Danos et al.

FOREIGN PATENT DOCUMENTS

| DE | 199 25 199 A1 | 12/2000 |
| DE | 100 59 631 A1 | 7/2002 |
| WO | WO 00/35479 | 6/2000 |
| WO | WO 01/97840 A1 | 12/2001 |

OTHER PUBLICATIONS

Pastrana et al., "NHPV16 VLP Vaccine Induces Human Antibodies That Neutralize Divergent Variants of HPV16," *Virology*, vol. 279, pp. 361-369 (2001).

Donnelly et al., "Protection against Papillomavirus with a Polynucleotide Vaccine," *Journal of Infectious Diseases*, vol. 713, pp. 314-320 (1996).

Giroglou et al., "Immunological analyses of human papillomavirus capsids," *Vaccine*, vol. 19, pp. 1783-1793 (2001).

Touze, et al., "The L1 Major Capsid Protein of Human Papillomavirus Type 16 Variants Affects Yield of Virus-Like Particles Produced in an Insect Cell Expression System," *J. Clin. Microbiol.*, vol. 36, No. 7, pp. 2046-2051 (Jul. 1998).

Kowalczyk et al., "Vaccine regimen for prevention of sexually transmitted infections with human papillomavirus type 16," *Vaccine*, vol. 19, pp. 3583-3590 (2001).

Schreckenberger et al., "Induction of an HPV 6bL1-specific mucosal IgA response by DNA immunization," *Vaccine*, vol. 19, pp. 227-233 (2001).

Sundaram et al., "Intracutaneous vaccination of rabbits with the cottontail rabbit papillomavirus (CRPV) L1 gene protects against virus challenge," *Vaccine*, vol. 15, No. 6/7, pp. 664-671 (1997).

Leder et al., "Enhancement of Capsid Gene Expression: Preparing the Human Papillomavirus Type 16 Major Structural Gene L1 for DNA Vaccination Purposes," *J. Virol.*, vol. 75, No. 19, pp. 9201-9209 (Oct. 2001).

Beitburd et al., "Human papillomavirus vaccines," *Cancer Biology*, vol. 9, pp. 431-445 (1999).

Roden et al., "Minor Capsid Protein of Human Genital Papillomaviruses Contains Subdominant, Cross-Neutralizing Epitopes," *Virology*, vol. 270, pp. 254-257 (2000).

Slupetzky et al, Chimeric papillomavirus-like particles expressing a foreign epitope on capsid surface loops, Journal of General Virology, (2001), 2799-2804, 82, Printed in Great Britian.

*Primary Examiner*—Ali R. Salimi
(74) *Attorney, Agent, or Firm*—Patterson, Thuente, Skaar & Christensen, P.A.

(57) ABSTRACT

A vaccine against disease caused by papilloma viruses is described in certain embodiments, as well as certain vectors, obtainable by the following methods: (a) one or more expression vectors that contain the DNA code for a structural protein of papilloma viruses or a fragment thereof are injected into mammals, whereby in at least some of the expression vectors randomly generated heterologous sequences are inserted into the DNA code (b) serums are obtained from the mammals and these are tested for the presence of antibodies against particles of various papilloma virus types, and (c) using the serums tested, the structural protein gene clones are identified that code for a polyvalent vaccine, and (d) the vaccine is produced from them. Procedures for producing a vaccine is also described, together with its use for vaccination against diseases caused by papilloma viruses.

13 Claims, No Drawings

POLYVALENT VACCINE AGAINST DISEASES CAUSED BY PAPILLOMA VIRUSES, METHOD FOR THE PRODUCTION AND THE USE THEREOF

CROSS REFERENCE TO RELATED APPLICATIONS

This application is a U.S. national stage application filed under 35 U.S.C. § 371 and claims priority to PCT/EP02/08360 (WO 03/01,1335), internationally filed Jul. 26, 2002, which claims priority to DE 101 37 102.0, filed Jul. 30, 2001, priority to which are claimed and which are hereby incorporated by reference herein.

BACKGROUND

The invention relates to polyvalent vaccines against diseases caused by papilloma viruses, the production process and application of the vaccines.

Papilloma viruses are a sub-family of papovaviruses with considerably more than 80 genotypes. Infection with papilloma viruses can lead to warts, papillomas, acanthomas, and skin and cervical carcinomas. A single illness can be caused by various papilloma virus types.

The capsids of the individual types of human pathogenic papilloma viruses (HPV) differ in their antigen characteristics (epitopes), meaning that after immunization with a specific HPV type, neutralizing antibodies cannot be induced against capsids of other HPV types. However such antibodies would be necessary to give comprehensive protection against diseases that can be caused by different HPV types.

An example is that infection with one of more than ten different HPV types can lead to cervical cancer. Although the virus particles of the individual types are very similar in their composition, they carry different neutralizing epitopes on their surface and are therefore only recognized by the immune system if there has been either a previous natural infection or vaccination with particles of the same type, and type-specific (neutralizing) antibodies are induced.

Vaccines for the effective prevention of diseases caused by HPV must therefore always contain a mixture of various virus types in order to give comprehensive protection. The production of such vaccines is however rendered more difficult owing to the fact described above, namely that one and the same disease can be caused by different HPV types.

To date only monovalent HPV vaccines have been developed, in other words vaccines directed against only one HPV type. However these have the serious disadvantage that they only guarantee protection against this one special HPV type, and not against other HPV types. Thus monovalent HPV vaccines do not furnish a comprehensive immune reaction.

SUMMARY AND DETAILED DESCRIPTION

Consequently the present invention is based on making a vaccine and also a process for its simple production available with which an immune response against different HPV types can be obtained.

According to the invention this is achieved by a vaccine against diseases caused by papilloma viruses, obtainable by the following method:

(a) One or more expression vectors are injected into mammals. These vectors contain the DNA code for a structural protein of papilloma viruses (PV) or a fragment thereof, whereby in the case of at least some of the expression vectors randomly generated heterologous sequences are inserted into the DNA code.

(b) serums are obtained from the mammals and these are examined for the presence of antibodies against particles of different papilloma virus types.

(c) using the serums examined the structural protein clones, particularly L1 clones, are identified that code for a polyvalent vaccine and (d) the vaccine is produced from them.

The expression "fragments thereof," as used above, indicates that the DNA codes for a protein that is shorter than the wild-type proteins, but which has the characteristics needed for this invention, especially the chemical, physical and/or functional characteristics.

When producing the vaccine according to the invention, the gene coding for PV capsids of a specific type, for example L1, can therefore be modified by inserting randomly generated sequences. Without prior production and cleaning of the capsids, for example by expression of the L1 gene using recombinant vectors such as plasmids, serums are produced through immunization with several L1 expression vectors that can be defined as pools of expression vectors, and these serums are then tested for reactivity with capsids of different PV types. Only after this are the pools isolated and in this way the capsids with cross-neutralizing epitopes identified.

As can be seen from the above detail the vaccine in accordance with the invention can be either VLPs (virus-like particles) or capsomeres containing modified L1 proteins that may indicate the presence of cross-neutralizing epitopes, in other words which lead to an antibody response directed against various different PV types. Such vaccines can be defined as polyvalent vaccines that can be used against infections with various PV types.

As explained above, DNA-free virus capsids, so-called virus-like particles (VLP), which accumulate in eucaryotic cells after the expression of the main structural protein L1, using recombinant vectors, may be suitable for the induction of neutralizing antibodies. VLPs are empty (free of nucleic acid) virus capsids produced using genetic engineering. Substructures of VLPs, too, known as capsomeres, which result from an incomplete assembly, for example when modified L1 molecules are present, contain neutralizing epitopes, which means they are suitable for producing vaccines in accordance with the invention.

Epitope is another term for antigen determinants. These are areas on the surface of an antigen where a specific antibody binds using its antigen-binding region.

To produce the vaccine according to the invention, a randomly generated heterologous sequence is inserted into a main structural protein, such as the L1 gene, of a specific papilloma virus type, especially into the hyper-variable regions of L1 genes.

The expression "insert" in the sense intended in this invention indicates that the randomly generated heterologous sequences could be present in the structural protein gene in addition to the naturally occurring epitopes, and/or that the naturally occurring epitope in the gene for the structural protein may be exchanged for a randomly generated heterologous sequence.

As an example the production of an L1 gene cassette will be described below, which enables various randomly generated oligo-nucleotides to be inserted into the hyper-variable areas of the L1 structural protein.

For inserting the randomly generated oligo-nucleotides into the DNA sequence of the L1 structural protein, a gene cassette can first be constructed. This gene cassette is characterized by the fact that, for example, the DNA code for the hyper-variable areas of the L1 structural protein is modified such that silent mutations are used to insert monovalent interfaces for restriction endonucleases, where the said interfaces flank these hyper-variable areas. The term 'silent mutation' is one used for the introduction of a modified DNA sequence that carries a recognition point for a specific restriction endonuclease without this changing the amino-acid sequence. The term 'monovalent interface' means a recognition sequence for a restriction endonuclease that occurs only once in the DNA sequence coding for the target protein. For technical reasons this has to be a recognition sequence for a restriction enzyme that may not be present additionally in the plasmids employed for the production of the variable DNA mixtures. The heterologous, randomly degenerated oligo-nucleotides may be constructed in such a way that they are also flanked by the monovalent interfaces, just as they flank the hyper-variable areas of the L1 DNA sequence. This way the gene cassette (in a cloning plasmid) and oligo-nucleotides can be treated with the same corresponding restriction enzymes. Ligation of the oligo-nucleotides into the gene cassette can then occur.

The expression "heterologous sequences", as used in this invention, refers to any sort of DNA sequence that differs from the coding DNA sequence for the naturally occurring epitope in the structural protein in at least one up to a maximum of all nucleotides. This can be achieved by replacing the nucleotides. Because epitopes usually only consist of a few amino-acids that are of the same size range as oligo-proteins, the heterologous sequences can be produced in the customary way, using the DNA sequences of the known epitopes as the basis, for example by oligo-nucleotide synthesis.

For example, if an epitope contains 12 amino acids, the corresponding DNA sequence will consist of 36 nucleotides. For the randomly generated heterologous sequences, one up to a maximum of all of these nucleotides can be substituted. Because one nucleotide can be replaced by a total of three other nucleotides differing from it, when DNA sequences are randomly generated a large number, up to several thousand, of new DNA sequences are created that are heterologous to the original DNA sequence. Because the production of this DNA is not site-specific, such as is the case when for example only one specific nucleotide in a DNA sequence is replaced, it can be defined as a randomly generated DNA sequence A so-called “random library” is an example of a collection of different, heterologous, randomly generated sequences.

Therefore in the case of the randomly generated heterologous DNA sequences employed to manufacture the vaccine in accordance with the invention we find they are ones not produced by site-specific mutations; rather, based on known epitope sequences, at least one nucleotide up to a maximum of all nucleotides are replaced in random fashion by one of the three other conceivable nucleotides, which gives rise to a randomly generated collection of a wide variety of DNA sequences. It is advantageous if the randomly generated heterologous DNA sequence is oriented to the naturally occurring epitopes in respect of the number of nucleotides, or ideally has the same number of nucleotides.

When manufacturing the randomly generated heterologous DNA sequences the DNA sequence of the wild type epitope is unavoidably obtained again through the random combining of the nucleotides.

Examples will be given below to show how randomly generated oligo-nucleotides are obtained. Oligo-nucleotides may be produced using the process of oligo-nucleotide synthesis. In this process the nucleotide sequence is produced linearly, in other words the extension of the chain occurs from the reaction of the already present nucleotide sequence with an active pre-stage of the following nucleotide. But to produce degenerated oligo-nucleotides not only the activated pre-stage of a nucleotide can be deployed; the activated pre-stages of 2, 3 or 4 nucleotides can also be introduced. This gives rise to oligo-nucleotide mixtures coding in this position for several different amino acids. If this process is repeated in subsequent stages of the reaction, a combination of different DNA sequences arises. Here both DNA sequences that do not occur in human pathogen PVs result, as well as the sequences that code for the wild-type epitope. As an example, for the main structural protein L1 the sequence area of amino acid 130 to 152 may apply (sequence numbering of HPV16L1). For the 23 amino acids of this sequence section a DNA sequence codes from 69 nucleotides. By also introducing the monovalent sequences, DNA sequences arise with more than 80 nucleotides. Alternatively the area of amino acids 260-299 or amino acids 349-360 may be selected. With complementary primers, different replenishing reactions with DNA polymerases can be used to synthesize the matching strand. The double-stranded DNA obtained this way can then be modified directly with the corresponding restriction endonucleases and ligated into the L1 gene cassette. To obtain greater efficiency the specialist may firstly ligate the double-stranded DNA sequences, using ‘blunt end’ clonings, into cloning vectors. From these ‘random libraries’ the DNA sequences can then be re-cloned with a high degree of efficiency into the L1 gene cassettes.

The randomly generated heterologous DNA sequences are then, as described above, inserted into the gene of the structural proteins of the PV, and in particular into the L1 gene of papilloma viruses of a specific type. HPV, BPV and CRPV are representative types of papilloma viruses. Particularly, insertion into the hyper-variable regions of L1 genes is carried out. The invention has been described here using the preferred structural protein gene L1, but it is not limited to this.

The length of the inserted heterologous DNA, in other words the number of nucleotides, is guided, as described above, by the length of the naturally occurring epitope. It is selected with particular care being taken not to interfere with the formation of the capsomeres and VLPs.

If the original epitopes of the L1 gene are replaced by the randomly generated heterologous DNA sequences, it may be that only one of the epitopes is replaced. However several, even all of the maximum possible epitopes in the L1 gene may be replaced by randomly generated heterologous sequences.

The L1 gene into which the randomly generated heterologous sequences are inserted may subsequently be cloned into eucaryotic expression vectors. In this case many bacterial clones may arise, and from this large number of bacteria clones sub-groups can then be formed. In other words this large number of bacteria clones is split up into pools of a few thousand bacteria clones and deployed for the production of vaccines in accordance with the invention.

To produce the vaccine in accordance with the invention one or more than one expression vector(s) are injected into mammals, whereby these vectors can be characterized as described above. The term ‘more than one’ here indicates that a pool of expression vectors can be used, containing up to 10,000, but particularly up to 5,000 expression vectors that differ from each other. The differences in the expression vectors then exist in particular in the randomly generated heterologous DNA cloned into them. As is clear from the above comments on randomly generated heterologous DNA, the expression vectors may also contain DNA sequences that were obtained when randomly generating the DNA sequences, but which—because the generation is also random in this case—are identical with the DNA sequence for the wild-type epitope. Consequently expression vectors are injected into the mammals where at least some, up to a maximum of all, of them contain randomly generated heterologous DNA sequences inserted into the DNA code.

These preselected pools are used for a DNA vaccination (genetic immunization). This consists of a recognized immunization procedure in which, unlike conventional immunizations, no antigens are injected; instead the DNA code is injected into a corresponding expression vector. The intramuscular application form has been shown to be favorable for DNA vaccination, because obviously in this case absorption and expression of the gene by the cell takes place before the DNA is broken down. The immune reaction then takes place in response to the expressed protein.

One advantage of DNA vaccination can be seen particularly in the fact that the virus particles no longer need to be manufactured and purified, for example by expression of the L1 gene using recombinant vectors. Thus DNA vaccination can be carried out simply and rapidly.

This DNA vaccination may be carried out on mammals such as rats, mice, hamsters and guinea pigs.

Serums can then be obtained from the test animals in the normal way, which are tested for reactivity with different types of papilloma virus. Testing can be done using ELISA, which are specific for papilloma virus types.

The DNA pools deployed for the DNA vaccination that provoke an immune reaction against different papilloma virus types can subsequently be isolated and again analyzed using DNA. In this way clones can be identified that code for VLPs or capsomeres and which contain cross-neutralizing epitopes. These are epitopes that lead to an antibody reaction against various papilloma virus types.

After this the corresponding DNA clones can be further examined using the customary procedures of genetic engineering, and, as the case may be, the corresponding virus particles produced, isolated and purified. Additionally L1 molecules, for example, can be expressed, VLPs or capsomeres can be produced and the immunity of the purified particles can be examined. Finally it is possible in this way to obtain the vaccine according to the invention, which is characterized by the fact that immunization against more than one papilloma virus type is possible. The vaccine according to the invention is, therefore, a multivalent vaccine that induces immune protection against diseases caused by different PV types.

In a preferred embodiment of the vaccine according to the invention the papilloma virus is a human pathogenic papilloma virus. This makes it possible to treat diseases caused by human pathogenic papilloma viruses with the vaccine according to the invention.

In another preferred embodiment the structural protein is L1, because this is particularly well suited for producing the vaccine according to the invention.

In another preferred embodiment the structural protein creates DNA-free virus capsids or capsomeres.

The object of this invention is also a DNA vaccine comprising one or more expression vector(s) containing the DNA code for a structural protein of papilloma viruses or a fragment thereof, wherein in at least some of the expression vectors randomly generated heterologous sequences are inserted into the DNA code.

As regards the structures and manufacture of the DNA vaccine reference should be made to the descriptions given above.

When administering the DNA vaccine according to the invention, the structural protein gene is expressed and immunization is carried out against the expressed protein. In this way immunization is achieved with particular ease.

The object of this invention is also a procedure to manufacture the vaccine described above, wherein
 (a) one or more expression vectors that contain the DNA code for a structural protein of papilloma viruses or a fragment thereof are injected into mammals, whereby in at least some of the expression vectors randomly generated heterologous sequences are inserted into the DNA code.
 (b) serums are obtained from the mammals and these are tested for the presence of antibodies against particles of various papilloma virus types, and
 (c) using the serums tested, structural protein gene clones, particularly L1 clones, are identified that code for a polyvalent vaccine, and
 (d) the vaccine is produced from them.

The individual steps of the procedure according to the invention have already been described in connection with the vaccine according to the invention, so reference is made to the respective embodiments.

The procedure according to the invention is characterized by the fact that the modified genes of the structural protein (insertion of randomly generated heterologous DNA) no longer have to be tested individually before immunization for their capacity to form VLPs or capsomeres. Instead, pools of recombinant DNA expression vectors are used to immunize mammals, in particular mice. The serums obtained are tested for the presence of antibodies against particles of various papilloma virus types, especially HPV types. If the reaction is positive, in other words if cross-neutralizing epitopes can be demonstrated, the pools of expression vectors are isolated and the corresponding proteins analyzed.

This procedure according to the invention enables the testing of a large number of variants of papilloma virus particles, especially capsids, for their immunogenic qualities, without having to express and purify the particles individually by expression of the mutated structural protein beforehand. Moreover, the procedure according to the invention enables the production of highly effective, multivalent papilloma virus vaccines quickly, simply and at a low cost.

The vaccine according to the invention is best suited as a polyvalent vaccine used in vaccinations against diseases caused by papilloma viruses, particularly diseases that are caused by more than one kind of papilloma virus. Examples of these diseases are warts, papillomas, acanthomas, and skin and cervical cancers.

The invention claimed is:
1. A method of making a polyvalent vaccine against a plurality of papilloma virus types, comprising:
  (a) injecting into at least one mammal a plurality of expression vectors, each expression vector comprising at least one papilloma virus L1 structural protein gene clone,
 wherein each L1 structural protein gene clone comprises DNA that encodes at least a portion of a L1 structural protein of a papilloma virus, and wherein the at least a portion of a L1 structural protein of a papilloma virus comprises at least one randomly generated heterologous sequence, which is derived from the coding sequence of a naturally occurring epitope by the substitution of one or more nucleotides and which substitutes the naturally occurring epitope sequence or which is present additionally to the naturally occurring epitopes of the L1 structural gene;

(b) obtaining serum from the at least one mammal, (c) testing the serum to detect antibodies against the particles of papilloma virus, and (d) identifying said at least one L1 structural protein gene clone that leads to an antibody response against a plurality of papilloma virus types.

2. The method of claim 1, wherein the papilloma virus is a human pathogenic papilloma virus.

3. The method of claim 1, wherein the particles of papilloma virus comprise DNA-free virus capsids.

4. The method of claim 1, wherein the particles of papilloma virus comprise capsomeres.

5. The method of claim 1, wherein the vaccine is a DNA vaccine that comprises at least one expression vector containing a DNA coding for at least a portion of a L1 structural protein of a papilloma virus, wherein the at least a portion of a L1 structural protein of a papilloma virus comprises at least one of the randomly generated heterologous sequences as defined in claim 1.

6. The method of claim 1 wherein the heterologous sequences have a length of between 6 and 200 bases.

7. The method of claim 1 wherein the structural protein is L1 protein, the structural protein gene clone comprises DNA that encodes for a hyper-variable portion of the L1 protein, and wherein the at least one randomly generated heterologous sequence comprises a heterologous sequence inserted into the hyper-variable portion of the L1 protein.

8. The method of claim 1, wherein the number of structural protein gene clones is between 10 and 10,000.

9. The method of claim 1, wherein the number of structural protein gene clones is at least 100.

10. A method of vaccination, the method comprising introducing a vaccine produced by the method of claim 1 into a mammal to vaccinate the mammal against a disease caused by a papilloma virus.

11. The method of claim 10, wherein the disease is a member of the group consisting of warts, papillomas, acanthomas, skin cancers, and cervical cancers.

12. The method of claim 1, further comprising producing the polyvalent vaccine using the at least one L1 structural protein gene clone that leads to an antibody response against a plurality of papilloma virus types.

13. The method of claim 1, wherein the at least one heterologous sequence is derived from the sequence encoding the naturally occurring epitope corresponding to amino acids 130 to 152 of the L1 protein.

* * * * *